US008272731B2

(12) United States Patent
Watanabe

(10) Patent No.: US 8,272,731 B2
(45) Date of Patent: Sep. 25, 2012

(54) IMAGE FORMING APPARATUS

(75) Inventor: Tatsuro Watanabe, Miyagi (JP)

(73) Assignee: Ricoh Company, Ltd., Tokyo (JP)

( * ) Notice: Subject to any disclaimer, the term of this patent is extended or adjusted under 35 U.S.C. 154(b) by 859 days.

(21) Appl. No.: 12/337,060

(22) Filed: Dec. 17, 2008

(65) Prior Publication Data

US 2009/0169222 A1 Jul. 2, 2009

(30) Foreign Application Priority Data

Dec. 28, 2007 (JP) ................................. 2007-340666

(51) Int. Cl.

*B41J 2/01* (2006.01)
*G01N 23/04* (2006.01)
*G03C 5/16* (2006.01)
*G21K 4/00* (2006.01)
*A61B 6/00* (2006.01)

(52) U.S. Cl. ......................... 347/104; 347/101; 250/582

(58) Field of Classification Search ........................ None
See application file for complete search history.

(56) References Cited

U.S. PATENT DOCUMENTS 4,344,614 A * 8/1982 Kaneko et al. ................ 271/288
7,784,891 B2 * 8/2010 Kumagai .......................... 347/8
7,950,757 B2 * 5/2011 Kumagai .......................... 347/8
2005/0231578 A1 * 10/2005 Tajima .......................... 347/104
2007/0007473 A1 * 1/2007 Kumagai ...................... 250/582
2007/0035605 A1 * 2/2007 Kitahara ....................... 347/104

FOREIGN PATENT DOCUMENTS

JP 2816217 8/1998
JP 2000-301710 10/2000
JP 2002-154711 5/2002
JP 2005-89125 4/2005
JP 2007-76175 3/2007
WO WO2006/054665 A1 5/2006

* cited by examiner

*Primary Examiner* — Matthew Luu
*Assistant Examiner* — Renee I Wilson
(74) *Attorney, Agent, or Firm* — Cooper & Dunham LLP

(57) ABSTRACT

An image-forming apparatus includes a recording head configured to eject ink droplets, a transport belt disposed facing the recording head and configured to transport a sheet, a suction mechanism to suctionally attract the sheet to the transport belt, a release mechanism configured to change a position of the transport belt between a home position close to the recording head and a release position away from the recording head, and a control mechanism configured to control transport and discharge of the sheet. The control mechanism, is configured to move the transport belt from the home position to the release position with the sheet being attracted to the transport belt when the control mechanism detects a sheet jam, rotate the transport belt in a direction in which the sheet is transported at the release position, and then discharge the sheet from the transport belt.

15 Claims, 6 Drawing Sheets

IMAGE FORMING APPARATUS

CROSS-REFERENCE TO RELATED APPLICATIONS

This patent specification claims priority from Japanese Patent Application No. 2007-340666, filed on Dec. 28, 2007 in the Japan Patent Office, the entire contents of which is hereby incorporated by reference herein.

BACKGROUND OF THE INVENTION

1. Field of the Invention

The present invention relates to an image-forming apparatus, and more particularly, to an image-forming apparatus that is equipped with a recording head for ejecting ink droplets and a transport belt for transporting sheets of recording media.

2. Discussion of the Background

As an image-forming apparatus, such as a printer, a facsimile machine, a plotter, or a multifunction machine including at least two of these functions, a liquid-ejecting image-forming apparatus such as an inkjet recording device that uses a recording head for ejecting ink droplets is known. It is to be noted that imaging, recording, and printing are synonymous with "image forming" in the descriptions below.

There are two types of the liquid-ejecting image-forming apparatus. A serial type image-forming apparatus forms images using a recording head that ejects ink droplets while moving in a main scanning direction. A line type image-forming apparatus forms images using a recording head that remains stationary while ejecting ink droplets.

In either case, the liquid-ejecting image-forming apparatus forms images by ejecting the ink droplets from the recording head onto a sheet while the sheet is being transported. Therefore, transport characteristics of the image-forming apparatus profoundly affect imaging performance.

One known liquid-ejecting image-forming apparatus is equipped with a transport unit that transports sheets while sucking air so as to draw the sheets to a transport belt using a suction fan disposed inside the transport belt.

Another known liquid-ejecting image-forming apparatus includes a transport unit to transport sheets using a transport belt, an image-recording unit such as a recording head that is equipped with several ink-ejecting ports aligned in the same direction as a direction in which the transport unit transports the sheets, and a release mechanism that switches the transport unit between an image-recording state and a release state to facilitate removal of jammed sheets. In the image-recording state, the transport unit can transport the sheets closes to the ink ejecting ports. In the release state, the transport unit is disengaged from all ink releasing ports and is almost parallel to or inclined with respect to the image-recording unit.

Another known liquid-ejecting image-forming apparatus includes a recording medium detector disposed in a transport path of the recording medium. When the recording medium detector detects jamming of the recording medium, the image-forming apparatus stops a transport unit that transports the recording medium, and determines whether or not jammed sheets can be automatically discharged. When the image-forming apparatus determines that the sheets can be automatically discharged, the image-forming apparatus automatically discharges, the recording medium to outside.

However, in an image-forming apparatus that transports sheets while suctionally attracting the sheets to the transport belt using a suction fan, a nozzle of the recording head might be damaged by contact with the sheets if the suction fan is stopped-immediately in case of a paper jam, because a force attracting the sheets to the surface of the transport belt then disappears.

Additionally, simply moving the transport belt to the releasing position distant from the recording head leaves the sheets on the transport belt, which must then be removed manually.

SUMMARY OF THE INVENTION

In view of the foregoing, one illustrative embodiment of the present invention provides an image-forming apparatus that includes a recording head configured to eject ink droplets, a transport belt disposed facing the recording head and configured to transport a sheet, a suction mechanism to suctionally attract the sheet to the transport belt, a release mechanism configured to change a position of the transport belt between a home position close to the recording head and a release position away from the recording head, and a control mechanism configured to control transport and discharge of the sheet. The control mechanism moves the transport belt from the home position to the release position with the sheet being attracted to the transport belt when the control mechanism detects a sheet jam, rotates the transport belt in a direction in which the sheet is transported at the release position, and then discharges the sheet from the transport belt.

Another illustrative embodiment of the present invention provides an image-forming apparatus-including the recording head, the transport belt, and the release mechanism described above. The image forming apparatus further includes a suction mechanism to suctionally attract the sheet to the transport belt and a control mechanism that moves the transport belt from the home position to the release position with the sheet being attracted to the transport belt when the control mechanism detects a sheet jam, and then cancel an attracting state in which the sheet is attracted to the transport belt.

Another illustrative embodiment of the present invention provides a method of controlling an image-forming apparatus that includes a recording head configured to eject ink droplets, a transport belt disposed facing the recording head and configured to transport a sheet, a suction mechanism to suctionally attract the sheet to the transport belt, and a release mechanism configured to change a position of the transport belt between a home position close to the recording head and a release position away from the recording head. The method includes detecting a sheet jam, moving the transport belt from the home position to the release position with the sheet being attracted to the transport belt when the sheet jam is detection, rotating the transport belt in a direction in which the sheet is transported at the release position, and discharging the sheet from the transport belt.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF PREFERRED EMBODIMENTS

Figure 1:
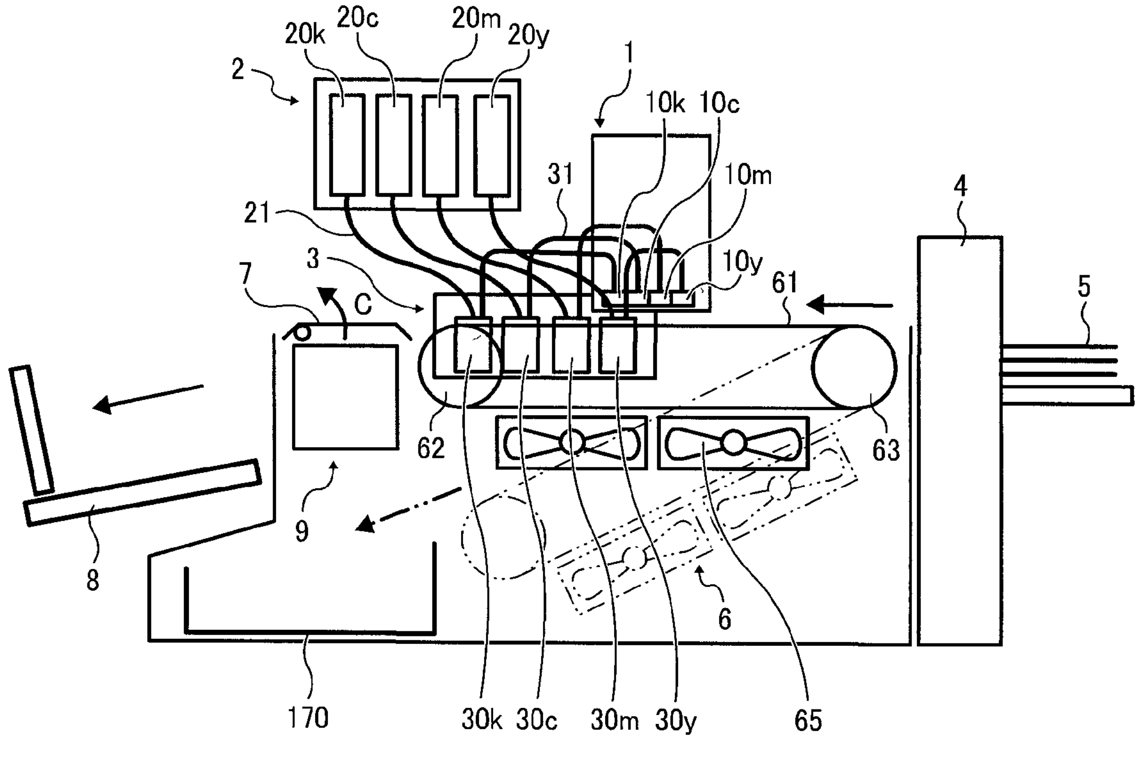
FIG. 1 is a schematic side view illustrating an overall configuration of an image forming apparatus according to one illustrative embodiment of the present invention.

In describing preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner and achieve a similar result.

It is to be noted that, in the present application, "image-forming apparatus" means the device that ejects the ink to a recording medium, such as paper, thread, fiber, textile, metal, plastic, glass, ceramic, etc., so as to form images thereon, and "image forming" includes both forming on the recording medium an image including a pattern, etc., that has no commonly understood meaning as well as image including a letter and/or an illustration that does have a given meaning. Further, "ink" is not limited to only the materials generally called "ink" but also used as a generic term for the liquid, such as recording-liquid, fixing liquid, other liquid, etc., that can form images.

Moreover, "transfer sheet" includes not only paper but also any materials onto which ink can adhere, such as, an overhead projector (OHP) sheet, textile, etc., and is used as a generic term for a recording medium, recording paper, a recording sheet, etc.

Figure 2:
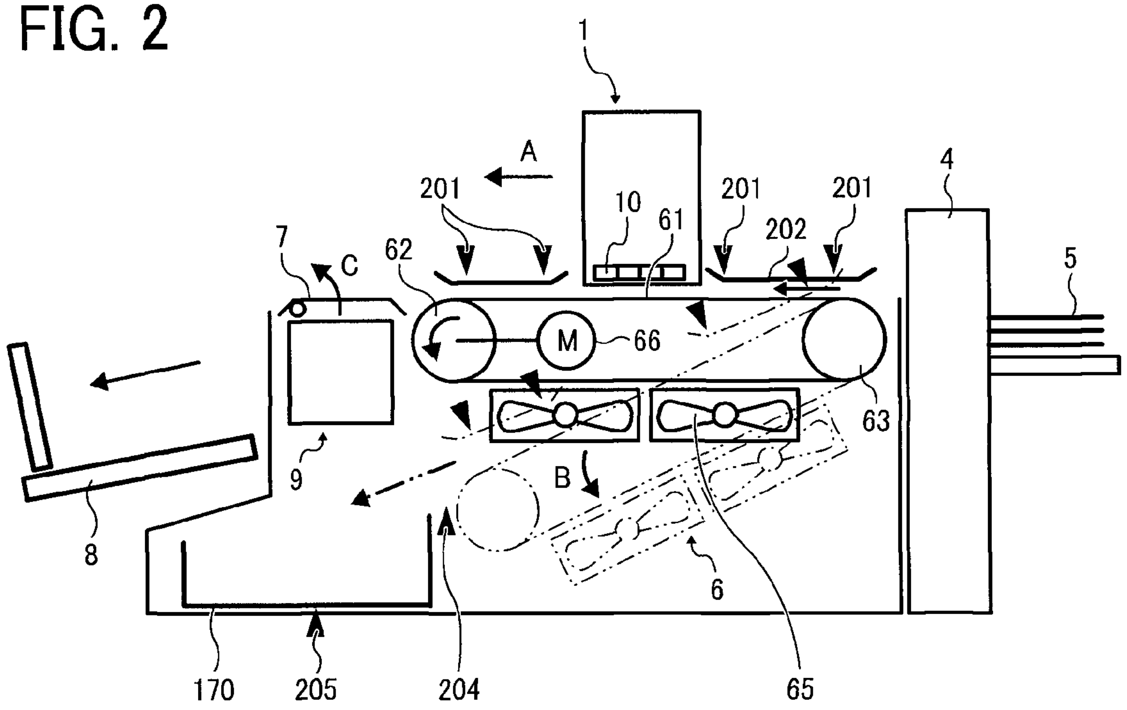
FIG. 2 is a schematic side view illustrating an ink supply part of the image forming apparatus shown in FIG. 1.
Figure 3:
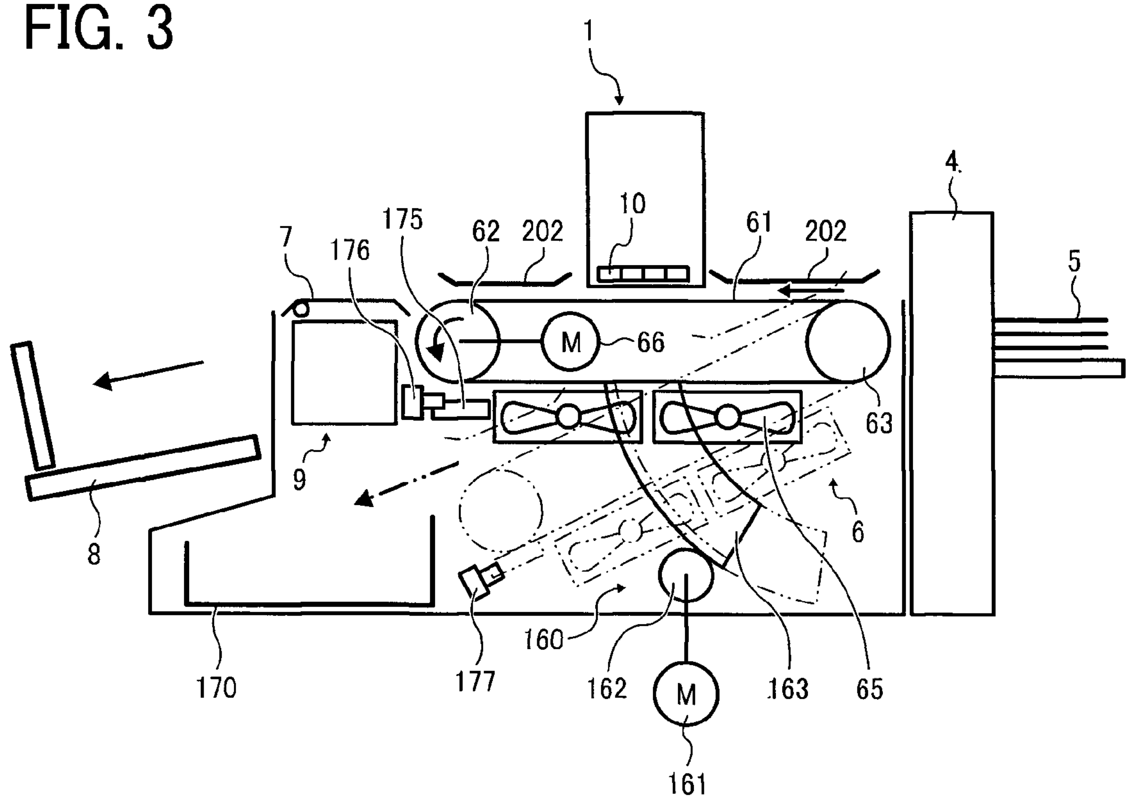
FIG. 3 is a schematic side view illustrating a configuration of a driving system that drives a transport unit of the image-forming apparatus shown in FIG. 1.

Referring now to the drawings, wherein like reference numerals designate identical or corresponding parts throughout the several views thereof, and particularly to FIGS. 1 through 3, an image-forming apparatus according to an illustrative embodiment of the present invention is described.

FIG. 1 is a schematic side view illustrating an overall configuration of the image-forming apparatus, FIG. 2 is a schematic side view illustrating an ink supply part thereof, and FIG. 3 is a schematic side view illustrating a driving system that drives a sheet transporting unit.

First, referring to FIG. 1, the image-forming apparatus is equipped with a head unit 1 including multiple recording heads 10*y*, 10*m*, 10C, and 10*k* held in a head-holder, not shown.

The multiple recording heads 10*y*, 10*m*, 10*c*, and 10*k* eject yellow, magenta, cyan, and black liquid ink, respectively.

The head unit 1 is movable in a direction indicated by arrow A in FIG. 2, in which the sheet is transported.

It is to be noted that the subscripts Y, M, C, and K attached to the end of each reference numeral indicate only that components indicated thereby are used for forming yellow, magenta, cyan, and black images, respectively, and hereinafter may be omitted when color discrimination is not necessary.

Referring to FIG. 1, the image forming apparatus is further equipped with an ink supply device is equipped with a main tank unit 2 and a sub tank unit 3. The main tank unit 2 includes replaceable main tanks 20, such as ink cartridges, storing respective color ink. The sub tank unit 3 includes sub tanks 30 for supplying the ink to the recording heads 10, respectively. The ink supply device supplies the respective color ink to the recording heads 10 in the head unit 1. The main tanks 20 connect to the sub tanks 30 through tubes 21 that supply ink, respectively.

It is to be noted that, because the sub tanks 30 in the sub tank unit 3 are located at a position lower than that of the recording heads 10 in the recording head unit 1 so as to balance the force of the ink to drip down from the recording heads 10 and the force of the ink to return to the sub tanks 30 through ink supply tubes 31, a required negative pressure is generated in the recording heads 10.

Beneath the recording head unit 1, a transport unit 6 disposed facing the head unit 1 transports a sheet 5 fed from a sheet feeder 4 is located.

The transport unit 6 includes a transport belt 61, a driving roller 62, a driven roller 63, a suction fan 65, a belt driving motor 66, a platen member, and so on.

On the transport belt 61, several suction holes for attracting the sheet 5 thereto by sucking air therethrough are formed so that the transport belt 61 can transport the sheet 5.

The transport belt 61 is wound around the driving roller 62 and the driven roller 63. As the driving roller 62 rotates, driven by the belt driving motor 66, the driven roller 63 is rotated, and thus the transport belt 61 is rotated.

The platen member, not shown, keeps the transport belt 61 flat. The suction fan 65 works as an attracting mechanism that sucks air from the attracting holes on the transport belt 61 so as to cause the sheet 5 to be attracted to the transport belt 61.

It is to be noted that attraction of the sheet is not limited to the sucking, alternatively, the sheet can be attracted to the transport belt 61 by electrostatic attraction, adhesion, etc.

A transport guide plate 7 is retractably located downstream from the transport belt 61 in a direction in which the transport belt 61 transports the sheet (hereinafter "sheet transport direction").

A discharge tray 8 is located downstream from the transport guide plate 7 in the sheet transport direction.

The image forming apparatus further includes a maintenance-recovery unit (cleaning unit) 9, located beneath the transport guide plate 7, that cleans the recording head 10, a release mechanism 160 that changes a position of the transport unit 6, and a jammed sheet tray 170 dedicated to the jammed sheet and located downstream from the transport unit 6 in the sheet transport direction.

Figure 4:
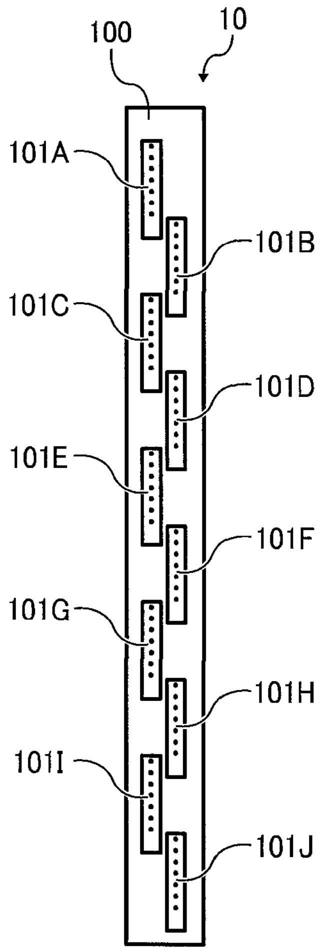
FIG. 4 is a plan view illustrating a configuration of a recording head according to one illustrative embodiment of the present invention.
Figure 5:
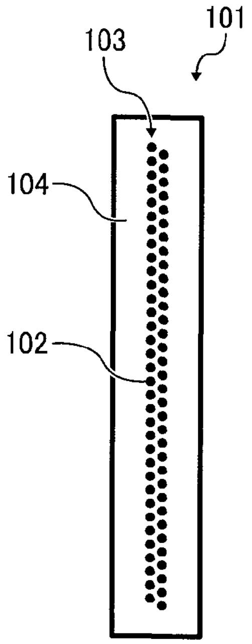
FIG. 5 is a plan view illustrating a configuration of a head unit according to one illustrative embodiment of the present invention.

A configuration of the recording head 10 is described below, using FIGS. 4 and 5. FIG. 4 is a plan view illustrating a configuration of a recording head. FIG. 5 is a plan view illustrating a configuration of a head unit.

As shown in FIG. 4, the recording head 10 includes ten heads 101A through 101J arranged in two alternating rows in a head support member 100. It is to be noted that the heads 101A through 101J all have an identical or similar configuration and thus hereinafter are simply referred to collectively as the head 101.

As shown in FIG. 5, each of the heads 101 has a nozzle face 104 including two nozzle lines 103 arranged in alternating rows. Each nozzle line 103 includes multiple nozzles 102 that eject ink droplets.

Maintenance and recovery, that is, cleaning, of the recording heads 10 is described below with reference to FIG. 1.

First, the transport guide plate 7 is rotated and opened in a direction indicated by arrow C shown in FIG. 1 so as to expose the topside of the cleaning unit 9.

Subsequently, the head unit 1 is slid and stopped above the cleaning unit 9.

After the nozzle face 104 of the recording head unit 1 is capped by a capping member, a pump sucking unit cleans the recording heads 10, by sucking the ink therein from the nozzles 102 through the capping member.

After the nozzle suction as the maintenance and recovery of the recording heads 10 is completed, the head unit 1 returns to a former printing position, and the transport guide plate 7 is closed. Thereafter, the image-forming apparatus can perform printing.

Referring to FIG. 2, the transport unit 6 can pivot on the driven roller 63 so as to move between a home position and a release position. The home position, which is also called a first position, is close to the recording unit 10, indicated by solid lines shown in FIG. 2. The release position, which is also called a second position, is away from the recording unit 10, indicated by broken lines shown in FIG. 2. At the release position, the driving motor 62 disposed on a downstream side is at a lower position than that of the driven motor 63 disposed on an upstream side in the sheet transport direction. Thus, the transport belt 61, the suction fan 65, etc., are pivotable between these two positions.

When the transport unit 6 is at the home position, the sheet 5 can be transported, and the head unit 1 can perform printing. On the other hand, when the transport unit 6 is at the release position, a sheet that is jammed in the transport unit 6 can be discharged.

Because a downstream portion of the transport unit 6 in the sheet transport direction pivotally moves down when the transport unit 6 moves to the release position, discharging the jammed sheet is relatively easy. Further, the head unit 1 can be prevented from touching the jammed sheet when the head unit 1 slides to the side of the cleaning unit 9 during jam correction.

Referring to FIG. 3, the release mechanism 160 causes the transport unit 6 to pivot and change its position between the home position and the release position and includes a motor 161 that releases the transport unit 6 (hereinafter a release mechanism driving motor 161), and a sector gear 163 to which torque from the release mechanism driving motor 161 is transmitted through a pinion gear 162.

The release mechanism driving motor 161 and the pinion gear 162 are fixed on a base of the image-forming apparatus, in other words, an apparatus frame, and the sector gear 163 is fixed on a unit frame, not shown, of the transport unit 6.

As the pinion gear 162 rotates, the sector gear 163 rotates, thereby enabling the transport unit 6 to pivot and change position.

It is to be noted that, although a timing belt, gear, etc., are used to transmit the rotation of the release mechanism driving motor 161 to the pinion gear 162, for simplicity those components are omitted in figures.

The jammed sheet tray 170 located downstream from the transport unit 6 in the sheet transport direction stocks only jammed sheets that are discharged from the transport unit 6 when the transport unit 6 is at the release position.

Further, a sensor filler 175 is attached to the driving motor 62 side of the transport unit 6, shown in FIG. 3. When the transport unit 6 is at the home position, a home position sensor 176 detects the sensor filler 175. By contrast, when the transport unit 6 is at the release position, a release position sensor 177 detects the sensor filler 175. In this way, whether the transport unit 6 is at the home position or the release position can be detected.

Next, referring to FIG. 2, four sheet sensors 201 that detect whether or not the sheet 5 is present in the transport unit 6 are disposed above the transport belt 61. The sheet sensors 201 are arranged in the sheet transport direction, along the center of the sheet in a width direction of the sheet.

It is to be noted that, as long as the sheet sensors 201 are able to detect that the sheet 5 remains on a transporting surface, that is, a surface of the transport belt 61 regarding any sheet size that the image-forming apparatus can accommodate, the location and number of such sensors are not limited to the configuration shown in FIG. 2, in which four sensors 201 are arranged in the sheet transport direction.

The sheet sensors 201 are attached to guide plates 202 disposed above the transporting surface, and the guide plates 202 are attached to the transport unit 6. When the transport unit 6 moves to the release position, the sheet sensors 201 move therewith, as indicated by the broken lines shown in FIG. 2.

Thus, the sheet sensors 201 can determine whether or not the sheet 5 is present on the transport belt 61 at the release position.

Additionally, a sheet-discharging sensor 204 is disposed downstream from the transport unit 6 when the transport unit 6 is at the release position. The sheet-discharging sensor 204 detects any jammed sheet that is in the process of being discharged onto the jammed sheet tray 170 from the transport unit 6.

Further, a jammed sheet tray sensor 205 that detects the jammed sheet in the jammed sheet tray 170 is provided on the jammed sheet tray 170.

When the jammed sheet tray sensor 205 detects that one or more jammed sheets are present in the jammed sheet tray 170, the jammed sheet tray sensor 205 reports that to a user. The jammed sheet tray sensor 205 is just a mechanism to report presence of the jammed sheet to the user, and thus, even when the jammed sheet tray sensor 205 detects the jammed sheet, a normal printing operation can be continued.

Figure 6:
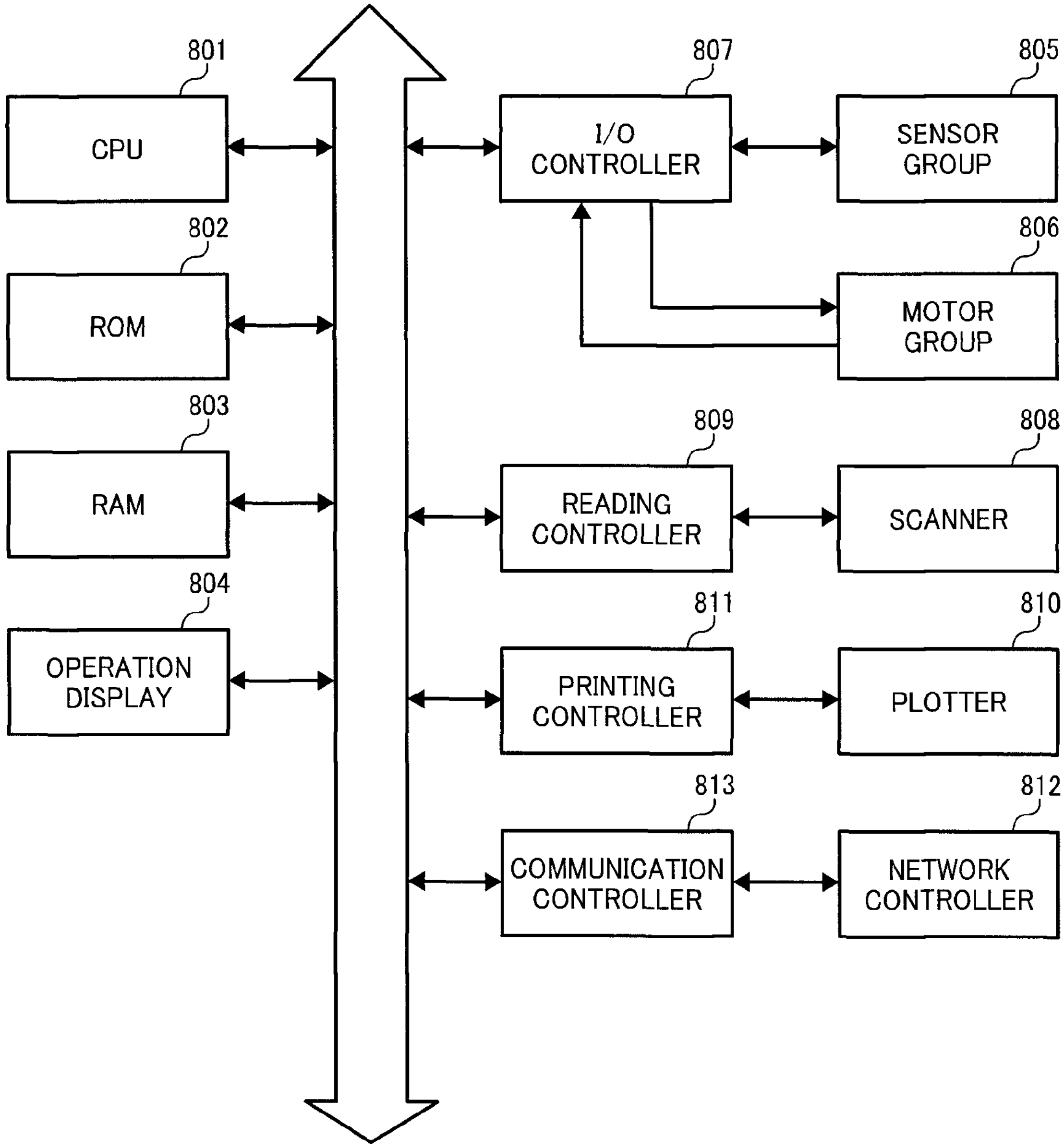
FIG. 6 is a block diagram of a controller of the image-forming apparatus.

Next, referring to the block diagram shown in FIG. 6, a controller of the image-forming apparatus is described below.

The controller includes a Central Processing Unit (CPU) 801, a Read Only Memory (ROM) 802, a Random Access Memory (RAM) 803, an operation display 804, a sensor group 805, a motor group 806, an Input Output (I/O) controller 807, a reading controller 809, a printing controller 811, a communication controller 813, etc.

The CPU 801 serves as a control mechanism that controls the image-forming apparatus according to the present invention. The ROM 802 stores information such as programs used by the CPU 801. The RAM 803 is used as a work area. On the operation display 804, an operator performs various settings.

The sensor group 805 includes the sheet sensor 201, the sheet-discharging sensor 204, and the discharging jammed sheet tray sensor 205, and detects a jammed sheet and the sheet size.

The motor group 806 includes the belt driving motor 66 that rotates the transport belt 61, and the releasing driving motor in the release mechanism.

The I/O controller 807 transmits output control signals to the sensor group 805 and the motor group 806.

The reading controller 809 controls a scanner 808 that is an image reading apparatus.

The printing controller 811 controls a plotter 810 that is a printing device.

The communication controller 813 controls various facsimile communications and a network controller 812 that controls an interface (IF) with telephone lines.

It is to be noted that, as described above, in an image-forming apparatus including a transport unit that transports sheets while suctionally attracting the sheets to the transport belt and a release mechanism that can disengage the transport unit from a recording head for ejecting ink droplets, a nozzle of the recording head might be damaged if a suction fan is stopped immediately in case of jamming.

More specifically, when a jam occurs while transporting the sheets and the sheets remain beneath the recording head, if the suction fan in the transport unit immediately stops, a force attracting the sheets to the surface of the transport belt disappears. Consequently, the sheets might touch the nozzle face of the recording head, damaging the nozzle and meniscus, and thus the nozzle becomes unable to eject next ink droplets.

Additionally, by only moving the transport belt to the releasing position distant from the recording head, the sheets remain on the transport belt, and thus, the user needs to remove the sheets manually to reset the image-forming apparatus.

Further, if the image-forming apparatus automatically discharges the jammed sheets onto the usual tray, the jammed sheets are mixed with the sheets on which images are successfully formed, necessitating a later sorting of the discharged sheets.

In view of the foregoing, a form of control of the image-forming apparatus according to the present embodiment that solves the foregoing problems is described below, with reference to a flow chart shown in FIG. 7 and a timing chart shown in FIG. 8. It is to be noted that the timing chart shown in FIG. 8 illustrates timing of operations performed when the image-forming apparatus determines that a sheet jam has occurred during image formation.

Figure 7:
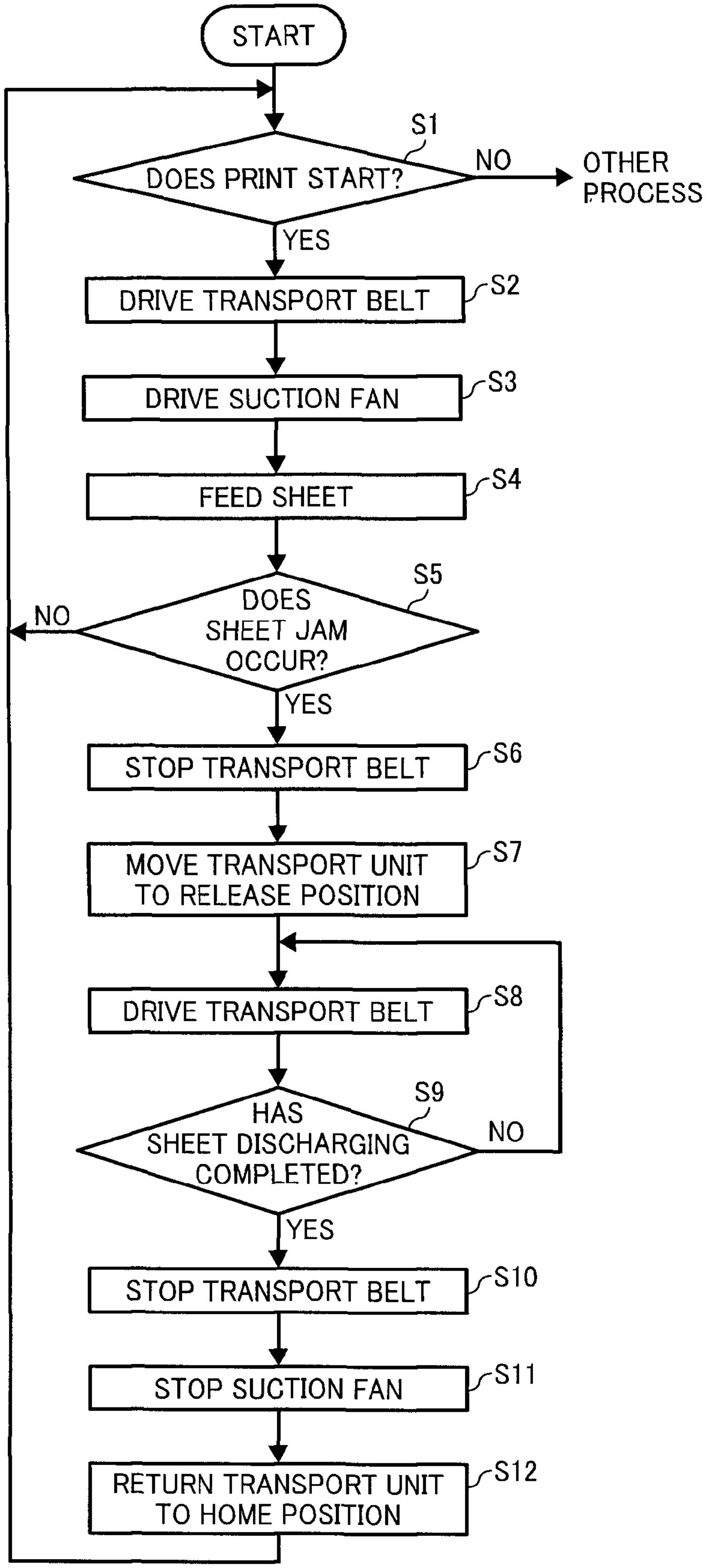
FIG. 7 is a flowchart illustrating an operation performed when a sheet jam occurs.

Initially, as shown in FIG. 7, at step S1 a print key is pushed, that is, printing is ON (time t0 in FIG. 8), and then, at S2, the transport belt 61 is rotated by the belt driving motor 66. At S3, the suction fan 65 begins to rotate. Then, at S4, sheet feeding is started.

Figure 8:
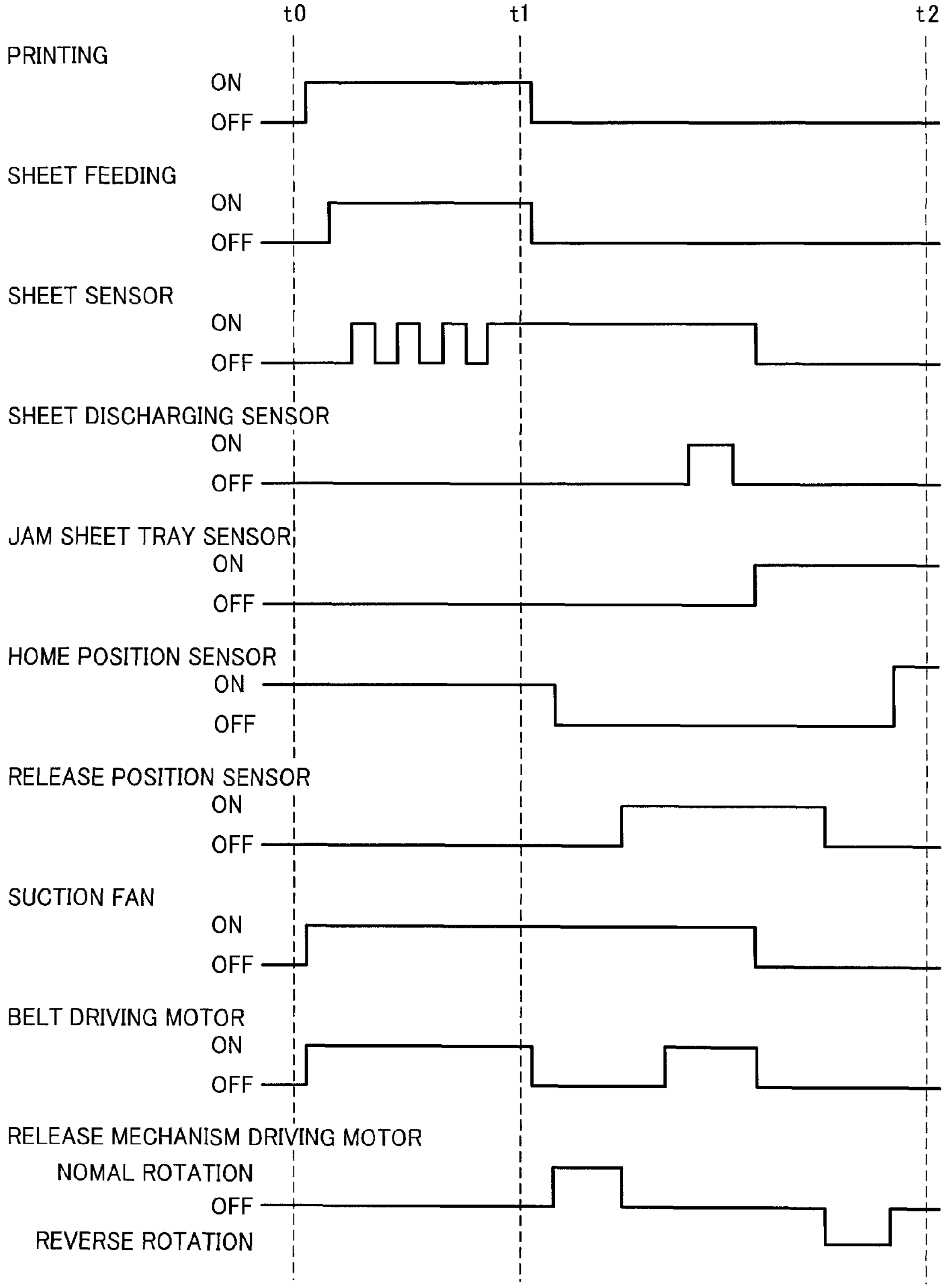
FIG. 8 is a timing chart illustrating the operation performed when the sheet jam has occurs.

Although feeding sheets is not shown in FIGS. 7 and 8, the sheets are transported onto the transport belt 61 of the transport unit 6 one by one.

While the sheet 5 is being transported on the transport belt 61, the sheet 5 passes beneath the sheet sensors 201. As a result, the sheet sensors 201 sequentially turn on and off each time the sheet 5 passes thereby.

At time t1 in FIG. 8, when the sheet sensor 201 detects a sheet jam while the sheet 5 is being transported, that is, during printing (YES at S5), printing is stopped (OFF), and therefore sheet feeding is also stopped.

At this time, although the transport belt 61 stops rotating at S6, the suction fan 65 keeps rotating.

It is to be noted that, in the example illustrated in the timing chart shown in FIG. 8, the sheet sensor 201 on the transporting unit 6 remains on, which shows that a sheet remains on the transport unit 6.

Subsequently, in order to disengage the transport unit 6 from the head unit 1, at S7 the release mechanism driving motor 161 begins normal rotation, and the home position sensor 176 turns off.

The release mechanism driving motor 161 continues to rotate until the release position sensor 177 turns on, thereby stopping the release mechanism driving motor 161.

At this time, because the suction fan 65 keeps running, the jammed sheet remains attracted to the transport belt 61. That is, with the jammed sheet attracted to the transport belt 61, the transport belt 61 pivots from the home position to the release position.

When the transport unit 6 thus reaches the release position, the sheet transport belt 61 starts to rotate at S8, thereby, discharging the jammed sheet on the transport belt 61 toward the jammed sheet tray 170.

Because the jammed sheet passes above the sheet-discharging sensor 204 while being discharged, the sheet-discharging sensor 204 confirms whether or not the jammed sheet is-discharged to the jammed sheet tray 170, after which the sheet sensor 201 on the transport belt 61 turns off. When the jammed sheet is successfully discharged to the jammed sheet tray 170, the jammed sheet tray sensor 205 turns back on.

It is to be noted that, although the timing chart shown in FIG. 8 shows the example in which the jammed sheet tray sensor 205 switches from OFF-mode to ON-mode, if a previous jammed sheet still remains on the jammed sheet tray 170, the jammed sheet tray sensor 205 remains in the ON-mode.

The jammed sheet tray sensor 205 is a detection mechanism designed to notify the user that the jammed sheet is stocked.

When the jammed sheet tray sensor 205 determinates that the jammed sheet is completely discharged onto the jammed sheet tray 170 (YES at S9), the transport belt 61 stops rotating at S10 and at S11, and the suction fan 65 stops rotating.

Subsequently, at S12, the transport unit 6 starts a return movement and pivots back to the home position.

In the return movement, the release mechanism driving motor 161 begins to rotate in reverse and keeps rotating until the home position sensor 176 turns on, that is, the transport unit 6 reaches the home position.

At time t2 in FIG. 8, printing is available when the home position sensor 176 is on, and printing is started when the next print start command is received. Printing remains enabled even if the jammed sheet is not removed from the jammed sheet tray 170, that is, the jammed sheet tray sensor 205 remains on.

Additionally, although not shown herein, as described above, while the transport unit 6 discharges the jammed sheet, the head unit 1 is slid to the side of the cleaning unit 9, and the recording heard 10 is cleaned by the cleaning unit 9, thereby enabling printing to restart with the recording head 10 clean.

In particular, when the image-forming apparatus is self-recoverable, that is, the image-forming apparatus automatically recovers and restarts printing from the required page after the transport unit 6 is moved to the release position and discharges the jammed sheet, stable printing can be kept or restarted.

As described above, the image-forming apparatus includes the transport belt disposed facing the recording head, a release mechanism, and a control mechanism.

The transport belt transports the sheet while attracting the sheet thereonto.

The release mechanism changes a position of the transport belt between the home position close to the recording head and the release position away from the recording head.

When the sheet jam is detected, the control mechanism moves the transport belt from the home position to the release position with the jammed sheet attracted to the transport belt and then cancels the attracting state.

Thus, when the sheet jam has occurred, the image-forming apparatus can reduce damage to the nozzle and meniscus, and can stably discharge the jammed sheet to the sheet tray dedicated to the jammed sheets.

Further, when the sheet jam is detected, the control mechanism moves the transport belt from the home position to the release position with the jammed sheet attracted to the transport belt, and then rotates the transport belt in the sheet transport direction at the release position so that the sheet on the transport belt is discharged.

Thus, when the sheet jam has occurred, the image-forming apparatus can reduce damage to the nozzle and meniscus, and can stably discharge the jammed sheet to the sheet tray dedicated to the jammed sheets.

Further, in the above-described embodiment, the sheet is attracted to the transport belt using the suction fan.

It is to be noted that, although the suction fan is stopped after the jammed sheet is completely discharged in the above-described embodiment of the present application, alternatively the suction fan can be stopped after the transport belt is rotated in the sheet transport direction for a predetermined distance at the release position with the jammed sheet attracted thereonto. More specifically, the transport belt is rotated with the sheet attracted thereonto from when the transport belt reaches the release position to when the sheet reaches a downstream end portion of a straight line on the transport belt in the sheet transport direction, and then the suction fan stops so as to cancel the attracting state, enabling the jammed sheet to dive under its own weight to the sheet tray dedicated to the jammed sheet.

Alternatively, the suction fan can be stopped while the transport belt is rotated in the sheet transport direction at the release position or after the transport belt reaches the release position. After the attracting state is canceled at the release position, the transport belt is rotated in the sheet transport direction. In this state, the jammed sheet remains on the transport belt under its own weight.

In this way, the jammed sheet can separate from the transport belt relatively easily and securely.

Further, although the above-described embodiment concerns a line type image-forming apparatus, alternatively, the present invention can also be applied to a serial type image-forming apparatus.

Numerous additional modifications and variations are possible in light of the above teachings. It is therefore to be understood that, within the scope of the appended claims, the disclosure of this patent specification may be practiced otherwise than as specifically described herein.

What is claimed is:

1. An image-forming apparatus, comprising:

a recording head configured to eject ink droplets;

a maintenance-recovery unit to clean the recording head;

a transport belt configured to transport a sheet, and having an upper surface disposed facing the recording head;

a release mechanism configured to change a position of the transport belt between a home position close to the recording head and a release position away from the recording head;

a home position sensor to detect a current position of the trans sort belt at the home position, and a release position sensor to detect the current position of the transport belt at the release position; and a control mechanism configured to control transport and discharge of the sheet and cleaning of the recording head, wherein the control mechanism moves the transport belt from the home position to the release position with the sheet on the transport belt when the control mechanism detects a sheet jam, after the transport belt is moved from the home position to the release position, the control mechanism causes the recording head to move to the maintenance-recovery unit in a direction in which the sheet is transported on the upper surface of the transport belt at the home position, and then causes the maintenance-recovery unit to clean the recording head;

the control mechanism rotates the transport belt in the direction in which the sheet is transported at the release position, and causes the transport belt to discharge the sheet from the transport belt;

the control mechanism returns the transport belt to the home position after the sheet is discharged from the transport belt at the release position and the recording head is cleaned by the maintenance-recovery unit.

2. The image-forming apparatus according to claim 1, further comprising a jammed sheet discharge tray to which a jammed sheet is discharged that is separate from a tray to which a proper sheet on which an image is properly formed is discharged.

3. The image-forming apparatus according to claim 1, wherein the control mechanism cancels an attracting state in which the sheet is attracted to the transport belt after the attracting state is kept as the transport belt is rotated for a predetermined distance in the direction in which the sheet is transported at the release position.

4. The image-forming apparatus according to claim 1, wherein the control mechanism continues to rotate the transport belt in the direction in which the sheet is transported after canceling the attracting state at the release position.

5. The image-forming apparatus according to claim 1, wherein the control mechanism returns the transport belt to the home position after the sheet is discharged from the transport belt at the release position.

6. The image-forming apparatus according to claim 5, wherein the recording head is cleaned while the transport belt moves from the home position to the release position and then returns to the home position.

7. The image-forming apparatus according to claim 1, further comprising a sensor to detect the sheet on the transport belt at the release position.

8. The image-forming apparatus according to claim 1, further comprising a suction mechanism to suctionally attract the sheet to the transport belt.

9. The image-forming apparatus according to claim 1, wherein the transport belt is wound around at least two rollers and is pivotable to the release position on the roller on an upstream. side in the direction in which the sheet is transported.

10. An image-forming apparatus comprising:

a recording head to eject ink droplet;

a maintenance-recovery unit to clean the recording head;

a transport belt configured to transport a sheet, and having an upper surface disposed facing the recording head;

a suction mechanism to suctionally attract the sheet to the transport belt;

a release mechanism configured to change a position of the transport belt between a home position close to the recording head and a release position away from the recording head;

a home position sensor to detect a current position of the transport belt at the home position, and a release position sensor to detect the current position of the transport belt at the release position; and a control mechanism configured to control transport and discharge of the sheet and cleaning of the recording head, wherein the control mechanism. moves the transport belt from the home position to the release position with the sheet being attracted to the transport belt when the control mechanism detects a sheet jam, after the transport belt is moved from he home position to the release position, the control mechanism causes the recording head to move to the maintenance-recovery unit in a direction in which the sheet is transported on the upper surface of the transport belt at the home position, and then causes the maintenance-recovery unit to clean the recording head;

the control mechanism causes the suction mechanism to cancel an attracting state, in which the sheet is attracted to the transport belt, at the release position to discharge the sheet from the transport belt; and the control mechanism returns the transport belt to the home position after the sheet is discharged from the transport belt at the release position and the recording head is cleaned by the maintenance-recovery unit.

11. A method of controlling an image-forming apparatus, the image-forming apparatus comprising:

a recording head configured to eject ink droplets;

a maintenance-recovery unit to clean the recording head;

a transport belt disposed facing the recording head and configured to transport a sheet, and having an upper surface disposed facing the recording head;

a suction mechanism to suctionally attract the sheet to the transport belt;

a release mechanism configured to change a position of the transport belt between a home position close to the recording head and a release position away from the recording head; and a home position sensor and a release position sensor, the method comprising:

detecting, by the home position sensor, a current position of the transport belt at the home position;

detecting a sheet jam;

moving the transport belt from the home position to the release position with the sheet being attracted to the transport belt when the sheet jam is detected;

detecting, by the release position sensor, the current position of the transport belt at the release position;

rotating the transport belt in a direction in which the sheet is transported at the release position to cause the transport belt to discharge the sheet from the transport belt at the release position while moving the recording head to the maintenance-recovery unit in the direction in which the sheet is transported on the upper surface of the transport belt at the home position and causing the maintenance-recovery unit to clean the recording head; and returning the transport belt from the release position to the home position.

12. The method according to claim 11, further comprising discharging a jammed sheet to a discharge tray separate from a tray to which a proper sheet on which an image is properly formed is discharged.

13. The image-forming apparatus according to claim 2, further comprising a sensor located in a downstream side of the transport belt to detect the jammed sheet in a process of the jammed sheet being discharged to the jammed sheet discharge tray.

14. The image-forming apparatus according to claim 2, further comprising a sensor to detect the jammed sheet in the jammed sheet discharge tray.

15. The image-forming apparatus according to claim 1, further comprising a sensor to detect the sheet on the transport belt wherein the sensor moves with the transport belt.

* * * * *